United States Patent [19]

Argoudelis et al.

[11] 4,259,450

[45] Mar. 31, 1981

[54] ANTIBIOTIC ACANTHOMYCIN AND PROCESS FOR PREPARING

[75] Inventors: Alexander D. Argoudelis, Portage; Thomas F. Brodasky, Kalamazoo; Fritz Reusser, Portage, all of Mich.

[73] Assignee: The Upjohn Company, Kalamazoo, Mich.

[21] Appl. No.: 772,552

[22] Filed: Feb. 28, 1977

[51] Int. Cl.$^3$ .......................... C12N 1/20; C12P 1/06; A61K 35/00
[52] U.S. Cl. .................................. 435/253; 435/169; 424/118; 424/124
[58] Field of Search ............. 195/80 R; 424/118, 124; 435/169, 253

[56] References Cited

U.S. PATENT DOCUMENTS 3,697,380 10/1972 Argoudelis et al. ............... 195/80 R

*Primary Examiner*—Alvin E. Tanenholtz
*Attorney, Agent, or Firm*—Roman Saliwanchik

[57] ABSTRACT

Antibiotic acanthomycin (U-53,827) produced by the controlled fermentation of the microorganism *Streptomyces espinosus* subsp. *acanthus*, NRRL 11081. This antibiotic and its base addition salts are active against Gram-positive bacteria. Accordingly, they can be used in various environments to eradicate or control such bacteria.

7 Claims, 2 Drawing Figures

ANTIBIOTIC ACANTHOMYCIN AND PROCESS FOR PREPARING

BRIEF SUMMARY OF THE INVENTION

The antibiotic of the invention, acanthomycin, is obtained by culturing the novel microorgaism *Streptomyces espinosus subsp. acanthus*, NRRL 11081, in an aqueous nutrient medium under aerobic conditions. Acanthomycin and its base addition salts have the property of adversely affecting the growth of Gram-positive bacteria, for example, *Staphylococcus aerueus* and *Streptococcus hemolyticus*. Accordingly, acanthomycin and its base addition salts can be used alone or in combination with other antibiotic agents to prevent the growth of or reduce the number of bacteria, as disclosed above, in various environments.

DETAILED DESCRIPTION OF THE INVENTION

Chemical and Physical Properties of Acanthomycin

Empirical Formula: $(C_{90}H_{139}N_{19}O_{42})_n$; Equivalent weight, 2,159.

Elemental Analysis:
Calcd.: C, 50.06; H, 6.48; N, 12.33; O, 31.12. Found: C, 49.81; H, 6.47; N, 12.36; O (by difference), 31.36.

Optical Rotation: $[\alpha]_D^{25}$, $-28.5°$ (c, 1, dimethylsulfoxide).

Solubilities: Acanthomycin free acid is soluble in dimethylformamide and dimethylsulfoxide. It is slightly soluble (ca. 1–2 mg/ml) in methanol and ethanol, and relatively insoluble in water, ether, halogenated hydrocarbon and saturated hydrocarbon solvents. Salts (ammonium and sodium) are soluble in water and lower alcohols.

Titration Data

Equivalent weight: 2,159
Titrant: KOH
Solvent: Dimethylformamide-60% aqueous ethanol (1:1).

Thin Layer Chromatography: On silica gel (Merck & Co.) using chloroform-ethanol-water (2:3:1 v/v), $R_f = 0.52$.

Figure 1:
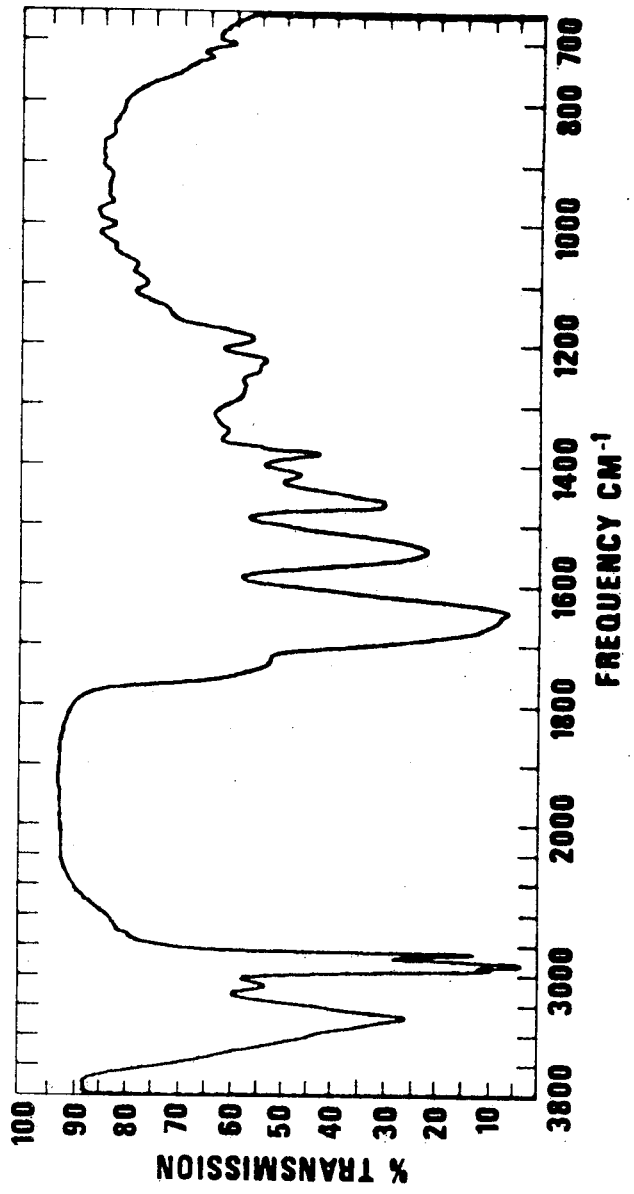

Infrared Absorption Spectra: Acanthomycin has a characteristic infrared absorption spectrum in a mineral oil mull as shown in FIG. 1 of the drawings. Peaks are observed at the following wave lengths expressed in reciprocal centimeters:

| Band Frequency (Wave Numbers) | Intensity |
| --- | --- |
| 3280 | S |
| 3070 | M |
| 2960 | S |
| 2930 | S |
| 3860 | S |
| 2650 | W |
| 1723 | M |
| 1656 | S, sh (sh = shoulder) |
| 1643 | S |
| 1540 | S |
| 1463 | S |
| 1415 | M |
| 1378 | M |
| 1341 | M |
| 1278 | M |
| 1268 | M |
| 1240 | M |
| 1223 | M |
| 1145 | W, sh |
| 1187 | M |
| 1098 | W |
| 1065 | W |
| 1033 | W |
| 1002 | W |
| 960 | W |
| 943 | W |
| 920 | W |
| 847 | W |
| 723 | W |
| 699 | M |

Key:
S = Strong, M = Medium, and W = Weak

Acanthomycin also has a characteristic infrared absorption spectrum when pressed in a KBr disc. Peaks are observed at the following wave lengths expressed in reciprocal centimeters:

| Band Frequency (Wave Numbers) | Intensity |
| --- | --- |
| 3390 | S, sh |
| 3290 | S |
| 3060 | M |
| 2960 | M |
| 2930 | M |
| 2880 | M |
| 2650 | W |
| 1724 | M, sh |
| 1652 | S |
| 1533 | S |
| 1455 | M |
| 1412 | M |
| 1385 | M |
| 1340 | M |
| 1273 | M |
| 1223 | M |
| 1183 | M |
| 1140 | M, sh |
| 1095 | W |
| 1067 | W |
| 1030 | W |
| 1000 | W |
| 960 | W |
| 920 | W |
| 875 | W |
| 737 | W |
| 698 | M |

Figure 2:
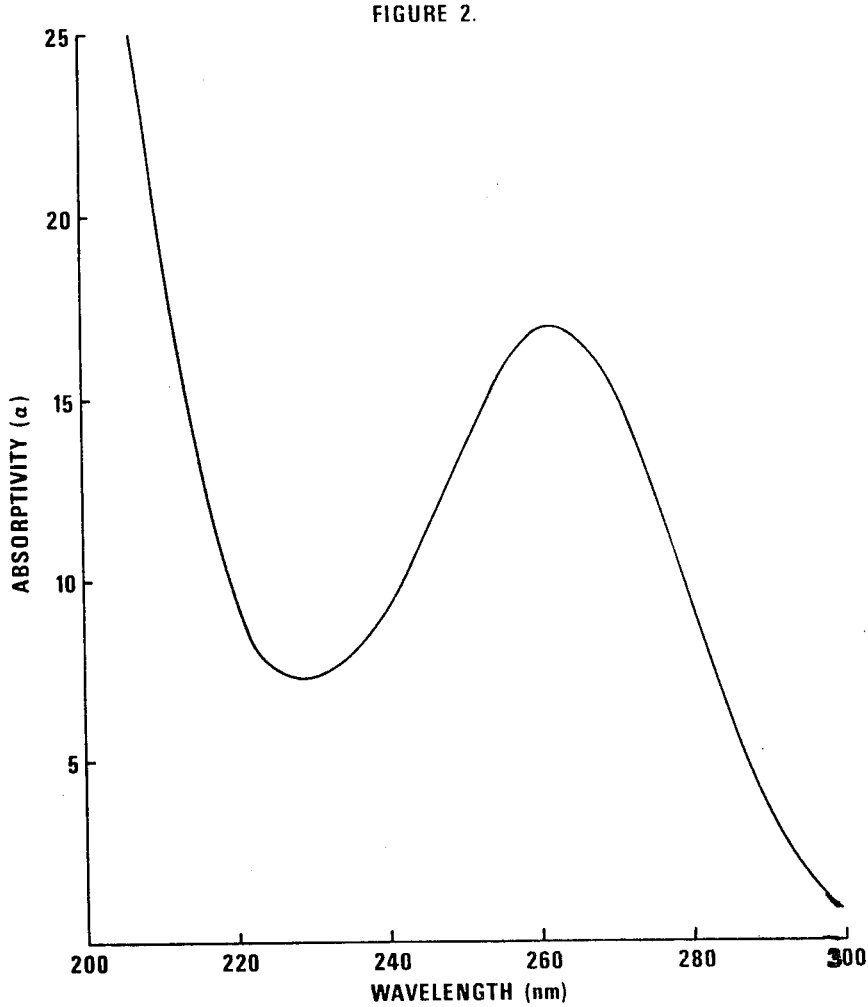

Ultraviolet Absorption Spectrum: Acanthomycin has a characteristic ultraviolet absorption spectrum in methanol as shown in FIG. 2 of the drawings. λ max at 262 (a=16.81) in methanol.

BIOLOGICAL PROPERTIES OF ACANTHOMYCIN

Acanthomycin was tested for antibacterial activity in a standard tube assay using nutrient broth as the medium. The minimum inhibitory concentration in mcg/ml against *S. aureus* was 50, and against *S. lutea* it was 25. Additional testing on a standard disc (12.7 mm) plate assay gave the following results:

| Acanthomycin mg/ml Concentration | Zone (mm) | | | | |
| --- | --- | --- | --- | --- | --- |
| | Streptococcus pyogenes | Staphylococcus aureus | Bacillus cereus | Bacillus subtilis | Sarcina lutea |
| 10 | 41.5 | 29.5 | 26 | 34 | 35 |

| Acanthomycin mg/ml Concentration | Strepto- coccus pyogenes | Staphylo- coccus aureus | Bacillus cereus | Bacillus subtilis | Sar- cina lutea |
|---|---|---|---|---|---|
| 5 | 40 | 28.5 | 25 | 33 | 34 |
| 2.5 | 40 | 28 | 23 | 31.5 | 32 |
| 1.25 | 38.5 | 26.5 | 21 | 30 | 30 |
| 0.62 | 36.5 | 24.5 | 20 | 28 | 27 |
| 0.31 | 34 | 22.5 | 17 | 26 | 25 |

Zone (mm) -continued

Acanthomycin was also tested in vivo in standard laboratory mice. *S. pyogenese* infected mice were protected by acanthomycin administered subcutaneously with a $CD_{50}$ of 0.23 (0.17–0.31) mg/kg. Against *S. aureus* infected mice the $CD_{50}$ was 1.0 mg/kg.

THE MICROORGANISM

The microorganism used for the production of acanthomycin is *Streptomyces espinosus* subsp. *acanthus*, NRRL 11081. A subculture of this microorganism is freely available from the permanent collection of the Northern Regional Research Laboratory, U.S. Department of Agriculture, Peoria, Ill., U.S.A. by request made thereto. It should be understood that the availability of the culture does not constitute a license to practice the subject invention in derogation of patent rights granted with the subject instrument by governmental action.

The microorganism of this invention was studied and characterized by Alma Dietz of the Upjohn Research Laboratories.

An actinomycete culture, isolated from a soil sample from southeast Texas was characterized as *Streptomyces espinosus* sp. n. in U.S. Pat. No. 3,697,380. Four additional soil isolates from southeast Texas soils had the same color pattern on Ektachrome as the type culture. In expanded studies the isolates were found to have the same sporophore and spore types as well as general cultural characteristics of the type culture. Outstanding characteristics of these cultures are their gray-green aerial growth, short sporophores bearing round spiny spores, and thermoduric growth. Differences in cultural characteristics (see Tables) and antagonistic properties are not sufficient to warrant variety designation of these new isolates. Three of these new isolates, which are disclosed in U.S. Pat. No. 3,833,475, have the accession numbers NRRL 5729, NRRL 5730 and NRRL 5731. The remaining isolate is described herein as *Stroptomyces espinosus* subsp. *acanthus*, NRRL 11081.

Methods for culture characterization were those cited by Dietz [Dietz, A. 1967. *Streptomyces steffisburgensis* sp. n. J. Bacteriol. 94: 2,022–2,026.] and in part those cited by Shirling and Gottlieb [Shirling, E. B., and D. Gottlieb. 1966. Methods for characterization of Streptomyces species. Int. J. Syst. Bacteriol. 16: 313–340.]. The cultures were also grown on Hickey-Tresner agar [Hickey, R. J. and H. D. Tresner. 1952. A cobalt-containing medium for sporulation of Streptomyces species. J. Bacteriol. 64: 891–892.] modified [Pepticase (enzymatic digest of casein) substituted for N-Z Amine A].

Color characteristics: Aerial growth gray-green. Melanin-negative. Appearance on Ektachrome [Dietz, A. 1954. Ektachrome transparencies as aids in actinomycete classification. Ann. N.Y. Acad. Sci. 60: 152–154.] is given in Table 1. Reference color characteristics are given in Tables 2 and 3. The cultures may be placed in the Green (GN) color series of Tresner and Backus [Tresner, H. D., and E. J. Backus. 1963. System of color wheels for streptomycete taxonomy. Applied Microbiol. 11: 335–338.].

Microscopic characteristics: Sporophores short, straight to flexuous, to open spiral to spiral (RF, RA, S) in the sense of Pridham et al. [Pridham, T. G., C. W. Hesseltine, and R. G. Benedict. 1958. A guide for the classification of streptomycetes according to selected groups. Placement of strains in morphological sections. Applied Microbiol. 6: 52–79.]. Spores mostly spherical with many showing a distinct linkage. Spore surface thorny to spiny in the sense of Dietz and Mathews [Dietz, A., and J. Mathews. 1971. Classification of Streptomyces spore surfaces into five groups. Applied Microbiol. 21: 527–533.]. Some spines show a transition to hairy. Spines are profuse and show markings when observed on spores treated by the carbon replica method of Dietz and Mathews [Dietz, A., and J. Mathews. 1962. Taxonomy by carbon replication. I. An examination of *Streptomyces hygroscopicus*. Applied Microbiol. 10: 258–263.].

Cultural and biochemical characteristics: Cultural and biochemical characteristics are cited in Table 4.

Carbon utilization: Growth of the cultures on carbon compounds was determined in the synthetic medium of Pridham and Gottlieb [Pridham, T. G., and D. Gottlieb. 1948. The utilization of carbon compounds by some Actinomycetales as an aid for species determination. J. Bacteriol. 56: 107–114.], Table 5 and in the synthetic medium of Shirling and Gottlieb, op. cit., 313–340, Table 6.

Temperature: Growth was fair at 18° C. and 55° C.; good at 24° C., and heavy at 28°–37° C. At 45° C. growth was fair (vegative) in 24 hours and heavy (good sporulation) in 72 hours. The agar media used were Bennett's, Czapek's sucrose, maltose-tryptone, and Hickey-Tresner (modified).

Antibiotic-producing properties: *S. espinosus* NRRL 5729, NRRL 5730, and NRRL 5731 produce the antibiotic lincomycin. *S. espinosus* subsp. *acanthus*, NRRL 11081, produces acanthomycin.

TABLE 1

Appearance of *Streptomyces espinosus* Cultures on Ektachrome*

| Agar Medium | Determination | NRRL 3890 | NRRL 5729 | NRRL 5730 | NRRL 5731 | NRRL 11081 |
|---|---|---|---|---|---|---|
| Bennett's | S | Gray-green | Gray-green | White to gray-green | Gray-green | Gray-green |
|  | R | Pale yellow-tan | Pale yellow-tan | Pale yellow | Pale yellow-tan | Pale yellow |
| Czapek's sucrose | S | Gray-green | Gray-green | Gray-green | Gray-green | Gray-green |
|  | R | Pale gray | Pale gray | Pale gray | Pale gray |  |
| Maltose-tryptone | S | Gray-green | Gray-green | Gray-green | Gray-green | Gray-green |
|  | R | Yellow-tan to | Yellow-tan to | Yellow | Yellow-tan | Pale yellow- |

TABLE 1-continued

Appearance of *Streptomyces espinosus* Cultures on Ektachrome*

| Agar Medium | Determination | NRRL 3890 | NRRL 5729 | NRRL 5730 | NRRL 5731 | NRRL 11081 |
|---|---|---|---|---|---|---|
| Peptone-iron | S | olive White | olive White | White | White | tan White |
| | R | Yellow | Yellow | Yellow | Yellow-tan | Yellow |
| 0.1% Tyrosine | S | Colorless | Colorless | Colorless | Gray-green | Gray-green |
| | R | Red | Red | Red | Red | Red |
| Casein starch | S | Gray-green | Gray-green | Gray-green | Gray-green | Gray-green |
| | R | Pale gray-green | Pale gray-green | Pale gray-green | Pale gray-green | Pale gray-green |

S = Surface
R = Reverse
*Dietz, A. 1954. Ektachrome transparencies as aids in actinomycete classification. Ann. N.Y. Acad. Sci. 60: 152–154.

TABLE 2

Reference Color Characteristics of *Streptomyces espinosus* Cultures

| Agar Medium | Determination | Color Harmony Manual, 3rd ed., 1948* | | | | |
|---|---|---|---|---|---|---|
| | | NRRL 3890 | NRRL 5729 | NRRL 5730 | NRRL 5731 | NRRL 11081 |
| Bennett's | S | a 2½fe 1½ge | a 2½ih 1ge | a 2½ih | 2½fe | 2½ih |
| | R | 1½ca 2fb 2ec | 1½ca 2fb 2ec | 1½gc | 2ec 1½ec | 2ea 2ic |
| | P | — | — | — | — | — |
| Czapek's sucrose | S | 1 li 2ig | 1 li 2ig | 2ig | 2ig | 2ig |
| | R | 1ec 2ig | 1ec 2ig | 2fe | 1ec | 2fe |
| | P | — | — | — | — | |
| Maltose-tryptone | S | 1ig 1½ge 1ih | 2½fe 1ih | 3ba 2½ih | 2½fe | 2½ih |
| | R | 2ge 2ec 2gc 1½ge | 2gc 1½ge | 2ic | 1½ie | 2ie |
| | P | — | — | — | — | — |
| Hickey-Tresner (modified) | S | 1ig | 1ig | 3ba 2½ih | 2½ih | 2½ih |
| | R | 2gc | 2ec | 2gc | 2gc | 2ec |
| | P | — | — | — | — | — |
| Yeast extract-malt extract (ISP-2) | S | 2½ih 2ih | 2½ih 2ih | 2½ih | 2½ih | 2½ih |
| | R | 2le 2gc | 2gc 2ie | 2le | 2gc | 2le |
| | P | — | — | — | — | — |
| Oatmeal (ISP-3) | S | 1ig 1½ig | 1ig 2fe | 2½fe | 2½ih | 2½fe |
| | R | 1ec 1½ge | 1ec 2ec | 2ec | 2ec | 2ec |
| | P | — | — | — | — | — |
| Inorganic-salts starch (ISP-4) | S | 2½ih 3ih | 2½ih 1ih | 2½ih | 2½ih | 2½ih |
| | R | 2ca 2gc | 2gc | 2gc | 2ec | 2gc |
| | P | 2ec | 2ec | 2ec | 2ig | 2ec |
| Glycerol-asparagine (ISP-5) | S | 1ig 2ih | a 2fe | 3ba 2½fe | 1½ig | 2½ih |
| | R | 1ec 2ge | 2gc 2ge | 2ge | 2ge | 2ig |
| | P | 2ge | — | — | — | — |

| Agar Medium | Determination | NBS Circular 553, 1955** | | | | |
|---|---|---|---|---|---|---|
| | | NRRL 3890 | NRRL 5729 | NRRL 5730 | NRRL 5731 | NRRL 11081 |
| Bennett's | S | 263gm 122gm 109gm | 263gm 122m 127g 109gm | 263gm 122m 127g | 122gm | 127g |
| | R | 89gm 87g 89m 90gm | 89gm 87g 89m 90gm | 102g 105gm | 90gm 90gm 93m | 86gm 87gm |
| | P | — | — | — | — | — |
| Czapek's sucrose | S | 110gm 110g | 110gm 112m | 110g 112m 94g | 110g 112m 121g | 110g 112m 94g |
| | R | 112m 121m 122g 110g | 112m 121m 122g 110g | 94g 112gm | 121g 122g | 94g 112gm |
| | P | 112m | 112m | — | — | — |
| Maltose-tryptone | S | 109gm 110g 109gm 112m 113g | 122gm 112m 113g | — 122m 127g | 122gm | 122m 127g |
| | R | 90gm 90gm 90gm 109gm | 90gm 109gm | 87gm | 106gm | 91gm 94g 106g |
| | P | — | — | — | — | — |
| Hickey-Tresner (modified) | S | 109gm 110g | 109gm 110g | — 127g | 122m 127g | 122m 127g |
| | R | 90gm | 90gm | 90gm | 90gm | 90gm |
| | P | — | — | — | — | — |
| Yeast extract-malt extract (ISP-2) | S | 122m 127g 122m 113g | 122m 127g 122m 113g | 122m 127g | 122m 127g | 122m 127g |
| | R | 88gm 94g 90gm | 90gm 91gm 94g | 88gm 94g | 90gm | 88gm 94g |
| | P | — | — | — | — | — |
| Oatmeal (ISP-3) | S | 109gm 110g | 109gm 110g 94g 112gm | 122gm | 122gm | 122gm |
| | R | 121m 109gm | 121m gm | 90gm | 90gm | 90gm |
| | P | — | — | — | — | — |
| Inorganic-salts starch (ISP-4) | S | 122m 113g 265m | 122m 112m 113g | 122m | 122m | 122m |
| | R | 89gm 90gm | 90gm | 90gm | 90gm | 90gm |
| | P | 90gm | 90gm | 90gm | 110g 112m | 90gm |
| Glycerol-asparagine (ISP-5) | S | 109gm 110g 112m 113g | 263gm 94g 112gm | — 122gm | — | 122m 127g |
| | R | 121m 122g | 90gm 94gm | 94g 109gm | 94m 109gm | 110g 112m |

TABLE 2-continued

Reference Color Characteristics of *Streptomyces espinosus* Cultures

|  | 94m | 109gm |  |  |  |
|---|---|---|---|---|---|
|  | 109gm |  |  |  |  |
| P | — | — | — | — | — |

S = Surface
R = Reverse
P = Pigment
m = matte
g = glossy
gm = glossy or matte surface of chip
*Jacobson, E., W.C. Granville, and C.E. Foss. 1948. Color harmony manual, 3rd ed. Container Corporation of America, Chicago, Illinois.
**Kelly, K.L., and D.B. Judd. 1955. The ISCC-NBS method of designating colors and a dictionary of color names. U.S. Dept. Comm. Circ. 553.

TABLE 3

Color Code for TABLE 2

| Color Harmony Manual, 3rd ed., 1948* | | NBS Circular 553, 1955** | |
|---|---|---|---|
| Color chip | Color name | Color chip | Color name |
| a | White | 263gm | White |
| 1ec | Light citron gray, putty | 121m | Pale yellow green |
|  |  | 122g | Grayish yellow green |
| 1ge | Citron gray | 109gm | Light grayish olive |
| 1ig | Olive gray | 109gm | Light grayish olive |
|  |  | 110g | Grayish olive |
| 1ih | Olive gray | 112m | Light olive gray |
|  |  | 113g | Olive gray |
|  |  | 127g | Grayish olive green |
| 1 li | Light olive drab | 110gm | Grayish olive |
| 1½ca | Cream | 89gm | Pale yellow |
| 1½ec | Biscuit, ecru, oatmeal, sand | 90gm | Grayish yellow |
|  |  | 93m | Yellowish gray |
| 1½gc | Dusty yellow | 102g | Moderate greenish yellow |
|  |  | 105gm | Grayish greenish yellow |

TABLE 3-continued

Color Code for TABLE 2

| Color Harmony Manual, 3rd ed., 1948* | | NBS Circular 553, 1955** | |
|---|---|---|---|
| Color chip | Color name | Color chip | Color name |
| 1½ge | Light olive gray | 109gm | Light grayish olive |
| 1½ie | Light olive | 106gm | Light olive |
| 1½ig | Olive gray | — | — |
| 2ca | Light ivory eggshell | 89gm | Pale yellow |
| 2ea | Light wheat, light maize | 86gm | Light yellow |
| 2ec | Biscuit, ecru, oatmeal, sand | 90gm | Grayish yellow |
| 2fb | Bamboo, buff, straw, wheat | 87g | Moderate yellow |
|  |  | 89m | Pale yellow |
| 2fe | Covert gray | 94g | Light olive brown |
|  |  | 122gm | Light olive gray |
| 2gc | Bamboo, chamois | 90gm | Grayish yellow |
| 2ge | Covert tan, griege | 94m | Light olive brown |
|  |  | 109gm | Light grayish olive |
| 2ic | Honey gold, light gold | 87gm | Moderate yellow |
| 2ie | Light mustard tan | 91gm | Dark grayish yellow |
|  |  | 94g | Light olive brown |
|  |  | 106g | Light olive |
| 2ig | Slate tan | 110g | Grayish olive |
|  |  | 112m | Light olive gray |
| 2ih | Dark covert gray | 112m | Light olive gray |
|  |  | 113g | Olive gray |
| 2le | Mustard, old gold | 88gm | Dark yellow |
|  |  | 94g | Light olive brown |
| 3ba | Pearl, shell tint | — | — |
| 3ih | Beige gray, mouse | 113g | Olive gray |
|  |  | 265m | Medium gray |
| 24½fe | Light mistletoe gray | 122gm | Grayish yellow green |
| 24½ih | Mistletoe gray | 122m | Grayish yellow green |
|  |  | 127g | Grayish olive green |

*Jacobson, E., W.C. Granville, and C.E. Foss. 1948. Color harmony manual, 3rd ed. Container Corporation of America, Chicago, Illinois.
**Kelly, K.L., and D.B. Judd. 1955. The ISCC-NBS method of designating colors and a dictionary of color names. U.S. Dept. Comm. Circ. 553.

TABLE 4

Cultural and Biochemical Characteristics of *Streptomyces espinosus* Cultures

| Medium | Determination | NRRL 3890 | NRRL 5729 | NRRL 5730 | NRRL 5731 | NRRL 11081 |
|---|---|---|---|---|---|---|
| Agar |  |  |  |  |  |  |
| Peptone-iron | S | Gray-white to gray-green | Gray-white to gray-green | Trace gray-green-white | Gray-green-white | Gray-green-white |
|  | R | Yellow | Yellow | Yellow | Yellow | Yellow |
|  | O | Melanin negative | Melanin negative | Melanin negative | Melanin negative | Melanin negative |
| Calcium malate | S | Fair to good gray-green | Trace gray-green | Trace gray-green | Trace gray-green | Trace gray-green |
|  | R | Pale gray | Pale gray | Pale gray | Pale gray | Pale gray |
|  | O | Malate not solubilized | Malate not solubilized | Malate not solubilized | Malate not solubilized | Malate not solubilized |
| Glucose-asparagine | S | Gray-white to gray-yellow | Gray-white to trace green | Fair gray-white | Fair gray-white | Fair gray-white |
|  | R | Light yellow to cream | Cream | Cream | Cream | Cream |
| Skim milk | S | White on edge to light gray-green yellow | White on edge to gray-green-pink | White on edge | White on edge | White on edge |
|  | R | Deep yellow to yellow-tan | Yellow-tan | Yellow-tan | Yellow-tan | Yellow-tan |
|  | O | Yellow to yellow-tan pigment Casein solubilized under growth to completely | Yellow-tan pigment Casein solubilized under growth to completely | Yellow-tan pigment Casein solubilized under growth | Yellow-tan pigment Casein solubilized under growth | Yellow-tan pigment Casein solubilized under growth |
| Tyrosine | S | Good to heavy gray-green | Good to heavy gray-green | Good gray-green | Good gray-green | Good gray-green |
|  | R | Red-tan to red-brown | Red-tan to red-brown | Red-tan | Red-tan | Red-tan |
|  | O | Red-tan to red-brown pigment Tyrosine solu- | Red-tan to red-brown pigment Tyrosine solu- | Red-tan pigment Tyrosine solu- | Red-tan pigment Tyrosine solu- | Red-tan pigment Tyrosine solu- |

TABLE 4-continued

Cultural and Biochemical Characteristics of *Streptomyces espinosus* Cultures

| Medium | Determination | NRRL 3890 | NRRL 5729 | NRRL 5730 | NRRL 5731 | NRRL 11081 |
|---|---|---|---|---|---|---|
| | | bilized | bilized | bilized | bilized | bilized |
| Xanthine | S | Good gray-green to good only on periphery | Good gray-green | Good gray-green | Good gray-green | Good gray-green |
| | R | Pale yellow to cream | Pale yellow-green to cream | Cream | Cream | Cream |
| | O | Xanthine not solubilized | Xanthine not solubilized | Xanthine not solubilized | Xanthine not solubilized | Xanthine not solubilized |
| Nutrient starch | S | Good gray-green | Good gray-green | Good gray-green | Good gray-green | Good gray-green |
| | R | Cream-olive | Cream-olive | Cream-olive | Cream-olive | Cream-olive |
| | O | Starch hydrolyzed | Starch hydrolyzed | Starch hydrolyzed | Starch hydrolyzed | Starch hydrolyzed |
| Yeast extract-malt extract | S | Good to heavy gray-green | Good gray-green | Good gray-green | Good gray-green | Good gray-green |
| | R | Pale yellow-tan to cream-yellow-tan | Cream-yellow-tan | Cream-yellow-tan | Cream-yellow-tan | Cream-yellow-tan |
| Bennett's | S | Cream to heavy gray-green | Gray-green-white to heavy gray-green | Trace gray-cream | Cream | Gray-green-white |
| | R | Yellow to olive | Cream to olive | Yellow | Yellow | Yellow-orange |
| Czapek's sucrose | S | Gray-green | Gray-green | Gray-green | Gray-green | Gray-green |
| | R | Gray-green | Gray-green | Gray-green | Gray-green | Gray-green |
| Maltose-tryptone | S | Heavy gray-green | Good to heavy gray-green | Gray-green-white | Pale gray-green | Gray-green white |
| | R | Olive to orange-yellow | Olive to cream | Yellow | Yellow-olive | Yellow-orange |
| Hickey-Tresner (modified) | S | Heavy gray-green | Heavy gray-green | Gray-green-white | Gray-green | Heavy gray-green |
| | R | Olive-orange | Cream | Deep yellow-tan | Yellow-olive | Olive-orange |
| Peptone-yeast extract-iron (ISP-6) | S | Cream to pale pink | Pale pink to gray-green | Cream to pale pink | Cream with trace gray-green to pale pink | Cream to pale pink |
| | O | Melanin negative | Melanin negative | Melanin negative | Melanin negative | Melanin negative |
| Tyrosine (ISP-7) | S | Gray-green-white to gray-green | Gray-green-white to gray-green | Gray-green | Gray-green | Gray-green |
| | R | Pale yellow-green to tan | Pale yellow-green to gray-cream | Gray-cream | Gray-cream | Gray-green |
| | O | Melanin-negative | Melanin-negative | Melanin-negative | Melanin-negative | Melanin-negative |
| Gelatin | | | | | | |
| Plain | O | Colorless vegetative growth to gray-white aerial growth; liquefaction ½ to complete | Colorless vegetative growth to gray-white aerial growth; liquefaction ½ to complete | Gray-white aerial growth; liquefaction complete | Gray-white aerial growth; liquefaction complete | Gray-green-white aerial growth; liquefaction complete |
| Nutrient | O | White to gray-white aerial growth; liquefaction ½ to complete | White to gray-white aerial growth; liquefaction ½ to complete | Gray white aerial growth; liquefaction complete | Trace gray-white aerial growth; liquefaction complete | Gray-white aerial growth; liquefaction complete |
| Broth | | | | | | |
| Synthetic nitrate | O | White to pink-cream aerial growth on surface pellicle; growth throughout medium; nitrate not reduced to nitrite | Trace white to pink-cream aerial growth on surface pellicle; growth throughout medium; nitrate not reduced to nitrite | Trace white aerial growth on surface pellicle; growth throughout medium; nitrate not reduced to nitrite | Trace white aerial growth on surface pellicle; trace growth throughout medium; nitrate not reduced to nitrite | Trace white aerial growth on surface pellicle; growth throughout medium; nitrate not reduced to nitrite |
| Nutrient nitrate | O | Gray-green-white aerial growth on surface pellicle; flocculent bottom growth; nitrate test: neither nitrate nor nitrite present or | Gray-green-white aerial growth on surface pellicle; flocculent bottom growth; nitrate not reduced to nitrate | Gray-green-white aerial growth on surface pellicle; flocculent bottom growth; nitrate not reduced to nitrite | Trace white aerial growth on surface pellicle; compact to flocculent bottom growth; nitrate not reduced to nitrite | Gray-green-white aerial growth on surface pellicle; flocculent bottom growth; nitrate not reduced to nitrite |

TABLE 4-continued

Cultural and Biochemical Characteristics of *Streptomyces espinosus* Cultures

| Medium | Determination | NRRL 3890 | NRRL 5729 | NRRL 5730 | NRRL 5731 | NRRL 11081 |
|---|---|---|---|---|---|---|
| | | nitrate not reduced to nitrite | | | | |
| Litmus milk | O | Cream to green aerial growth on yellow to tan surface ring; litmus reduced; peptonization; pH 7.3 | Pink-tan to gray-green aerial growth on surface ring; litmus reduced; peptonization; pH 7.3 | Tan aerial growth on surface ring; litmus reduced; peptonization pH 7.3 | Green-white aerial growth on surface ring; partial reduction; partial peptonization; pH 7.1 | Tan aerial growth on surface ring; partial reduction; partial peptonization; pH 7.4 |

S = Surface
R = Reverse
P = Pigment
O = Other Characteristics

TABLE 5

Utilization Of Carbon Compounds By *Streptomyces espinosus* Cultures In The Synthetic Medium Of Pridham And Gottlieb*

| | NRRL 3890 | NRRL 5729 | NRRL 5730 | NRRL 5731 | NRRL 11081 |
|---|---|---|---|---|---|
| CONTROL | (+)** | (−)** | (+) | (+) | (+) |
| 1. D-Xylose | + | + | + | + | + |
| 2. L-Arabinose | + | + | + | + | + |
| 3. Rhamnose | + | + | + | + | + |
| 4. D-Fructose | + | (+),+ | + | + | + |
| 5. D-Galactose | + | + | + | + | + |
| 6. D-Glucose | + | + | + | + | + |
| 7. D-Mannose | + | + | + | + | + |
| 8. Maltose | + | + | + | + | + |
| 9. Sucrose | (+) | (−),(+) | (+) | (+) | (+) |
| 10. Lactose | + | + | + | + | + |
| 11. Cellobiose | + | + | + | + | + |
| 12. Raffinose | (+) | (−) | (+) | (+) | (+) |
| 13. Dextrin | + | + | + | + | + |
| 14. Inulin | (+),(−) | (−) | (+) | (+) | (+) |
| 15. Soluble starch | + | + | + | + | + |
| 16. Glycerol | + | + | + | + | + |
| 17. Ducitol | (+),(−) | (−) | (+) | (+) | (+) |
| 18. D-Mannitol | + | + | + | + | + |
| 19. D-Sorbitol | +,(−) | (−) | + | + | + |
| 20. Inositol | + | (+) | + | + | + |
| 21. Salicin | (+) | (+) | + | (+) | (+) |
| 22. Phenol | (+),(−) | (−) | (+) | (+) | (+) |
| 23. Cresol | − | − | − | − | − |
| 24. Na Formate | (+),− | (−)− | (+) | (+) | (+) |
| CONTROL | (+)** | (−)** | (+) | (+) | (+) |
| 25. Na Oxalate | (+),(−) | (+),(−) | (+) | (+) | (+) |
| 26. Na Tartrate | (+),(−) | (−),− | (+) | (+) | (+) |
| 27. Na Salicylate | − | − | − | − | − |
| 28. Na Acetate | (+) | (+) | (+) | (+) | (+) |
| 29. Na Citrate | + | (+) | + | (+) | + |
| 30. Na Succinate | (+),(−) | (−) | (+) | (+) | (+) |

+ = Good utilization
(+) = Poor utilization
(−) = Doubtful utilization
− = No growth
*Pridham, T.G., and D. Gottlieb. 1948. The utilization of carbon compounds by some Actinomycetales as an aid for species determination. J. Bacteriol. 56: 107–114.
**Results from different studies

TABLE 6

Utilization Of Carbon Compounds By *Streptomyces espinosus* Cultures In The Synthetic Medium Of Shirling And Gottlieb*

| | NRRL 3890 | NRRL 5729 | NRRL 5730 | NRRL 5731 | NRRL 11081 |
|---|---|---|---|---|---|
| CONTROL | | | | | |
| Negative-basal medium | ±** | −,±** | ± | ± | ± |

TABLE 6-continued

Utilization Of Carbon Compounds By *Streptomyces espinosus* Cultures In The Synthetic Medium Of Shirling And Gottlieb*

| | NRRL 3890 | NRRL 5729 | NRRL 5730 | NRRL 5731 | NRRL 11081 |
|---|---|---|---|---|---|
| Positive-basal medium plus D-glucose | + | + | + | + | + |
| Carbon compounds | | | | | |
| L-Arabinose | ±,++ | ±,+ | ± | ± | ± |
| Sucrose | − | ±,− | − | − | − |
| D-Xylose | ++ | ±,++ | ++ | ++ | ++ |
| Inositol | ++ | ±,+ | ++ | ++ | ++ |
| D-Mannitol | ++ | ++ | ++ | ++ | ++ |
| D-Fructose | ++ | ±,+ | ++ | ++ | ++ |
| Rhamnose | ++ | ++ | ++ | ++ | ++ |
| Raffinose | − | − | − | − | − |
| Cellulose | +,++ | ±,− | + | + | + |

++ Strong utilization
± Utilization doubtful
+ Positive
− Utilization negative
*Shirling, E.B., and D. Gottlieb. 1966. Methods for characterization of *Streptomyces* species. Int. J. Syst. Bacteriol. 16: 313–340.
**Results from different studies The new compound of the invention is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation medium since tap water and unpurified ingredients are used as components of the medium prior to sterilization of the medium.

Production of the compound of the invention can be effected at any temperature conductive to satisfactory growth of the microorganism, for example, between about 18° and 40° C., and preferably between about 20° and 28° C. Ordinarily, optimum production of the compound is obtained in about 3 to 15 days. The medium normally remains neutral during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the new compound and the attendant inefficient utilization of the equipment. Accordingly, it is desirable to produce a vegetative inoculum in a nutrient broth culture by inoculating this broth culture with an aliquot from a soil stock, an agar plug stored above liquid $N_2$, or a slant culture. When a young, active vegetative inoculum has thus been secured, it is transferred aseptically to large vessels or tanks. The medium in which the vegetative inoculum is produced can be the same as, or different from, that utilized for the production of the new compound, so long as good growth of the microorganism is obtained.

A variety of procedures can be employed in the isolation and purification of the compound of the subject invention, for example, solvent extraction, partition chromatography, silica gel chromatography, liquid-liquid distribution in a Craig apparatus, adsorption on resins, and crystallization from solvents.

In a preferred recovery process the compound of the subject invention is recovered from the culture medium by separation of the mycelia and undissolved solids by conventional means, such as by filtration or centrifugation. The antibiotic is recovered from the filtered or centrifuged broth by extraction with a suitable solvent for acanthomycin, for example, water-immiscible alcohols like 1-butanol (preferred). The solvent extract containing the desired antibiotic is concentrated and then subjected to purification procedures as disclosed infra.

Before disclosing purification procedures, there is first disclosed alternate recovery procedures. Acanthomycin can be recovered from the fermentation whole beer by filtration followed by adsorption of the antibiotic on a non-ionic resin. Suitable non-ionic resins include resins comprising a non-ionic macro porous copolymer of styrene crosslinked with divinylbenzene. Non-ionic resins of this type, marketed under the trade names Amberlite XAD-2 and XAD-4, are disclosed in U.S. Pat. No. 3,515,717.

Further, activated carbon, alumina and related adsorbants can be used to recover acanthomycin from filtered fermentation beer.

Since acanthomycin is an acidic compound, anion exchangers, for example, Dowex-1; Dowex-2; Dowex 21K (Dow Chemical Co., USA) or Amberlite IRA-900; -IRA-904; -IR-45 (Rohm and Haas Co., USA) can be used to recover the antibiotic from filtered fermentation beer. The antibiotic is adsorbed onto the resin and then eluted by the use of an aqueous solution of inorganic acids, salts like ammonium chloride and bases like ammonium hydroxide, dilute sodium hydroxide, and the like.

After recovery of acanthomycin from the fermentation beer, the recovery preparation is then subjected to purification procedures which will ultimately yield a purified crystalline preparation of acanthomycin. It should be recognized, however, that any of the crude preparations containing acanthomycin, including the fermentation beer, can be used for purposes well known to those skilled in the antibiotic art. For example, such crude preparations can be used as feed for animals. Where relatively pure preparations of acanthomycin are desired, the crude preparaions of acanthomycin can be purified by the following procedures, or obvious equivalents thereof.

The crude preparation of acanthomycin is first mixed with a suitable solvent, for example, ethyl acetate, and the like, to precipitate a material containing acanthomycin. This material is isolated by filtration and then distributed between water and a suitable solvent for acanthomycin, for example, 1-butanol. The solvent phase containing acanthomycin, is separated out, then mixed with water. The pH of the mixture is adjusted to a basic pH, for example, about 7.9, with concentrated base, for example, ammonium hydroxide. The resulting solvent and aqueous phases are separated and then the aqueous phase is extracted with a solvent for acanthomycin. The solvent extract containing acanthomycin is then subjected to chromatographic procedures on a suitable resin, for example, Amberlite IRA-904 anion exchanger in the chloride form. This resin is a product of Rohm and Haas Company, USA. The chromatographic resin column is eluted with aqueous ammonium chloride.

Active fractions from the above chromatographic procedure are then subjected to another chromatographic procedure to separate acanthomycin from ammonium chloride. The resin used in this procedure is a non-ionic resin known as Amberlite XAD-7, again a product of Rohm and Haas Co. This resin is eluted with a methanol-water mixture to give fractions containing acanthomycin. The active fractions are combined and then concentrated to an aqueous and freeze-dried to give a relatively pure preparation of acanthomycin.

A highly purified preparation of acanthomycin can be obtained by subjecting the above-described freeze-dried preparation to chromatography using DEAE-Sephadex (A-25) supplied by Pharmacia Fine Chem., Uppsala, Sweden. The preparation containing acanthomycin is dissolved in ammonium chloride and this solution is then passed over a column containing the DEAE-Sephadex (A-25). Fractions active against B. subtilis and S. pyogenes are pooled. Acanthomycin is isolated from the resulting three pools by use of chromatographic procedures using a non-ionic resin, for example, Amberlite XAD-7.

In processing the pools over the Amberlite XAD-7 resin, the resin is eluted with a methanol-water mixture to give acanthomycin. The ammonium salt of acanthomycin is made by adjusting the pH of these fractions to about 7.5 with ammonium hydroxide.

Acanthomycin is active against S. aureus and can be used to disinfect washed and stacked food utensils contaminated with these bacteria; it can also be used as a disinfectant on various dental and medical equipment contaminated with S. aureus. Further, acanthomycin and its salts can be used as a bacteriostatic rinse for laundered clothes, and for impregnating papers and fabrics; and, they are also useful for suppressing the growth of sensitive organisms in plate assays and other microbiological media. Since acanthomycin is active against B. subtilis, it can be used in petroleum product storage to control this microorganism which is a known slime and corrosion producer in petroleum products storage.

It is to be understood that the microbiological process disclosed herein, though described in detail with reference to *Streptomyces espinosus* subsp. acanthus, NRRL11081, is not limited to this particular microorganism deposit. It is intended that any microorganism meeting the cultural characteristics disclosed herein, or substantial equivalents thereof, wherever deposited in the world, is a part of the subject microbiological process. Further, it is intended that this invention include strains or mutants of the said microorganism which can be produced by procedures well known in the art, for example, by subjecting the novel microorganism to x-ray or ultraviolet radiation, nitrogen mustard, phage exposure, and the like.

Since acanthomycin is an acidic compound, it forms salts with both inorganic and organic bases. For example, the sodium, potassium, ammonium, calcium, and the like, salts can be made by neutralizing a solution of acanthomycin in aqueous methanol. Salts of acanthomycin with organic bases (primary, secondary and tertiary amines) for example, pyridine, piperidine, and the like, can be made by mixing of equal molar amounts of acanthomycin and the desired organic base.

The following examples are illustrative of the process and products of the subject invention but are not to be construed as limiting. All percentages are by weight and all solvent mixture proportions are by volume unless otherwise noted.

EXAMPLE 1

Part A. Fermentation

An agar slant of *Streptomyces espinosus* subsp. acanthus, NRRL 11081, is used to inoculate a series of 500-ml Erlenmeyer flasks, each containing 100 ml of sterile preseed medium consisting of the following ingredients:

| | |
|---|---|
| Glucose monohydrate | 25 g/liter |
| Pharmamedia* | 25 g/liter |
| Tap water q.s. | 1 liter |

*Pharmamedia is an industrial grade of cottonseed flour produced by Traders Oil Mill Company, Fort Worth, Texas.

The preseed medium presterilization pH is 7.2. The preseed inoculum is grown for three days at 28° C. on a Gump rotary shaker operating at 250 r.p.m. and having a 2½ inch stroke.

Preseed inoculum (300 ml), prepared as described above, is used to inoculate a seed tank containing 20 liters of sterile seed medium consisting of the following ingredients:

| | |
|---|---|
| Glucose monohydrate | 25 g/liter |
| Pharmamedia | 25 g/liter |
| Tap water | Balance |

The inoculated seed medium is incubated at a temperature of 28° C. for 2 days while being agitated at a rate of 400 r.p.m. and aerated at a rate of 10 standard liters per minute with a back pressure of 10 psig.

After 2 days incubation, the seed medium is used to inoculate (the inoculation rate is 5 liters of seed inoculum per 100 liters of fermentation medium) a 250 liter fermentation tank containing sterile fermentation medium consisting of the following ingredients:

| | |
|---|---|
| B and F Distillers Solubles* | 40 g/liter |
| NaCl | 5 g/liter |
| NaNO₃ | 10 g/liter |
| Ucon** | 2 ml/liter |
| Tap water q.s. | Balance |
| pH - 7.0 (presterilization) | |

*Distillers residue supplied by Brown-Forman Distillers Corp., P.O. Box 1080, Louisville, KY 40201.
**a synthetic defoamer supplied by Union Carbide, N.Y., N.Y.

The fermentation tank is incubated at a temperature of 28° C., with agitation of 200 r.p.m. and aeration at 150 standard liters per minute with back pressure at 10 psig. Harvest is usually after 3 to 12 days of fermentation.

The fermentation can be monitored by a disc-plate assay using *B. subtilis* as the test organism and deionized H₂O as diluent. A unit volume (0.08 ml) of solution containing the substance to be assayed is placed on a 12.7 mm paper disc which is then placed on an agar plate seeded with the assay organism. The agar plate is then incubated for 16 to 18 hours at 32° to 37° C. A biounit (BU) is defined as the concentration of the antibiotic which gives a 20 mm zone of inhibition under the standard assay conditions. Thus, if for example a fermentation beer has to be diluted 1/100 to give a 20 mm zone of inhibition, the potency of such beer is 100 BU/ml.

Part B. Recovery

Whole fermentation beer (ca. 5,000 l), obtained as described above, is adjusted to pH 2.75 with 6 N aqueous hydrochloric acid. The adjusted whole beer is then filtered using filter aid (diatomaceous earth). The mycelial cake is washed with 1,000 l of water. The washed filter cake is discarded. The aqueous wash is combined with the clear filtrate and the resulting solution (5,750 l) is extracted with 1,600 l of 1-butanol. The spent beer is discarded. The butanolic extract is concentrated to a volume of ca. 8 l (4.5 kg). This material is designated preparation ADA-117A.

Part C. Purification

(No. 1) Precipitation

One liter of preparation ADA-117A, isolated as described in the recovery section is poured into 10 l of ethyl acetate under stirring. The mixture is stirred at room temperature for one hour. The precipitated material containing acanthomycin is isolated by filtration and treated as described, infra under distribution.

(No. 2) Distribution

The precipitate is distributed between 2.5 l of water and 2.5 l of 1-butanol. The butanol phase (ADA-31C) is mixed with 7 l of water. The pH of the mixture is adjusted to 7.9 with concentrated ammonium hydroxide. The two phases are separated and designated Butanol-1 and Aqueous-1. Aqueous-1 is then extracted 3 times with 2.5 l portions of 1-butanol each time at pH 7.9 (adjusted with ammonium hydroxide). The three butanolic extracts (designated Butanol-2, Butanol-3-and Butanol-4) are combined with Butanol-1 and the combined extract is kept as ADA-31D.

Testing for bioactivities showed the following:

| Preparation | Zone (mm) | | | | |
|---|---|---|---|---|---|
| | S. pyogenes | B. cereus | S. aureus | B. subtilis | S. lutea |
| ADA-31C | 36 | 18 | 20 | 23 | 27 |
| ADA-31D | 36 | 16 | 24 | 26.5 | 27 |

Preparation ADA-31D containing most of the bioactivity was treated as described below.

(No. 3) Amberlite IRA-904 Chromatography

The column is prepared from 2 liters of Amberlite IRA-904 anion exchanger in the chloride form. (Product of Rohm and Haas, USA).

The butanolic extract (ADA-31D), obtained above, is mixed with one half of its volume of methanol and one half of its volume of water and this solution is passed through the column at a rate of 50–70 ml/minute. The spent is collected in three equal fractions designated "Spent-1," "Spent-2" and "Spent-3" which are found bioinactive.

The column is washed with 6 l of water. This eluate, kept as "Aqueous," is found bioinactive.

The column is then eluted with 2% aqueous ammonium chloride. Fractions of 20 ml are collected and combined in 500 ml fractions and tested. Results follow. Zone size in mm.

| Fraction No. | S. pyogenes | B. cereus | S. aureus | B. subtilis | S. lutea |
|---|---|---|---|---|---|
| 1 | 0 | 0 | 0 | 0 | 0 |
| 2 | 0 | 0 | 0 | 0 | 0 |
| 3 | 35 | 17 | 25 | 26.5 | 25 |
| 4 | 39 | 21 | 27.5 | 30 | 29 |
| 5 | 40 | 22 | 28.5 | 31 | 30 |
| 6 | 39 | 21 | 28 | 29.5 | 29.5 |
| 7 | 39 | 20.5 | 27.5 | 29.5 | 28.5 |
| 8 | 38 | 20 | 27 | 29 | 28.5 |
| 9 | 37 | 20 | 27 | 28.5 | 28.5 |
| 10 | — | 18 | 25 | 28 | 28 |
| 11 | — | 16.5 | 24 | 27.5 | 27.5 |
| 12 | — | 16 | 23 | 26.5 | 26.5 |
| 13 | — | 15.5 | 23 | 25.5 | 25 |
| 14 | — | 15.5 | 22.5 | 24.5 | 24.5 |
| 15 | — | traces | 21 | 22.5 | 23 |
| 16 | — | 0 | 18 | 18 | 17 |
| 17 | — | 0 | 0 | 0 | 0 |
| 18 | — | — | — | — | — |

Fractions 3–18 are combined, adjusted to pH 5.5 with 6 N aqueous hydrochloric acid and this solution is used as starting material for the chromatography described below.

(No. 4) Amberlite XAD-7 Chromatography

Separation of Acanthomycin from Ammonium Chloride

The column is prepared from 2 l of Amberlite XAD-7 (Rohm and Haas Co., USA).

The solution described above containing acanthomycin in mixture with ammonium chloride (8 l, pH 5.5) is passed over the column at a rate of 80–100 ml/minute. The spent is collected in two equal fractions designated "Spent-1" and "Spent-2".

The column is washed with 4 l of water (flow rate 80–100 ml/minute). Four equal fractions (Aqueous-1; -2; -3; -4) are collected.

The column is then eluted with methanol-water (70:30 v/v). Fractions of 20 ml are collected. Testing shows the following. Zone size in mm.

| Fraction | S. pyogenes | S. aureus | B. cereus | B. subtilis | S. lutea |
|---|---|---|---|---|---|
| Start-Material | 35 | 24.5 | 19 | 27.5 | 26 |
| Spent-1 | 0 | 0 | 0 | 0 | 0 |
| Spent-2 | 0 | 0 | 0 | 0 | 0 |
| Aqueous-1 | 0 | 0 | 0 | 0 | 0 |
| Aqueous-2 | 0 | 0 | 0 | 0 | 0 |
| Aqueous-3 | 0 | 0 | 0 | 0 | 0 |
| Aqueous-4 | 0 | 0 | 0 | 0 | 0 |
| MeOH-Water | | | | | |
| 10 | 0 | 0 | 0 | 0 | 0 |
| 20 | 0 | 0 | 0 | 0 | 0 |
| 80 | 0 | 0 | 0 | 0 | 0 |
| 90 | 42 | 29 | 23.5 | 35.5 | 37 |
| 100 | 40 | 28.5 | 24 | 33 | 35 |
| 110 | 30 | 19.5 | traces | 22.5 | 24 |
| 120 | 24 | traces | 0 | 17.5 | 17 |
| 130 | 21.5 | 0 | 0 | traces | traces |
| 140 | 18 | 0 | 0 | 0 | 0 |
| 150 | 15.5 | 0 | 0 | 0 | 0 |
| 160 | 16 | 0 | 0 | 0 | 0 |
| 170 | 15 | 0 | 0 | 0 | 0 |
| 180 | traces | 0 | 0 | 0 | 0 |
| 190 | 0 | 0 | 0 | 0 | 0 |
| 200 | 0 | 0 | 0 | 0 | 0 |
| 250 | 0 | 0 | 0 | 0 | 0 |

Fractions 85–125 are combined. The solution is concentrated to an aqueous and freeze-dried to give preparation ADA-34.1, 3.7 g containing acanthomycin.

Using 5.5 l of preparation ADA-117A, obtained as described in Part B., supra, as the starting material, and using the above-described purification procedure (precipitation, distribution, IRA-904 and XAD-7 chromatographies) a total of 21.71 g of material of highly active acanthomycin is obtained (Prep. ADA-113.4).

Highly purified acanthomycin, obtained as described above, is purified by DEAE-Sephadex chromatography as shown below.

(No. 5) DEAE-Sephadex Chromatography

Eight hundred g of DEAE-Sephadex (A-25) (Pharmacia Fine Chem., Uppsala, Sweden) is slurried in 0.05 N ammonium chloride solution adjusted to pH 8.5 with ammonium hydroxide. The mixture is allowed to stand at room temperature for 12 hours. The swelled resin is then poured into a column. The column is then washed with 25 l of solvent.

The starting preparation, ADA-113.4 (20 g), obtained as described above, is dissolved in 200 ml of the 0.05 N ammonium chloride (pH 8.5) solvent and this solution is added on the top of the column. The column is then eluted with the same solvent. Fractions are tested for bioactivity against B. subtilis and S. pyogenes. Results follow.

| Fraction No. | Volume (l) | Zone (mm) | |
|---|---|---|---|
| | | B. subtilis | S. pyogenes |
| 1 | 2.0 | 0 | 0 |
| 2 | 2.0 | 0 | 0 |
| 3 | 8.5 | 0 | 0 |
| 4 | 12.0 | 0 | 0 |
| 5 | 4.0 | 0 | 0 |
| 6 | 4.0 | 0 | 0 |
| 7 | 3.0 | 0 | 0 |
| 8 | 12.0 | 0 | 0 |

-continued

| Fraction No. | Volume (1) | Zone (mm) B. subtilis | S. pyogenes |
|---|---|---|---|
| 9 | 4.0 | 15 | 24 |
| 10 | 3.5 | 17 | 28 |
| 11 | 9.0 | 20 | 28 |
| 12 | 7.5 | 21 | 28.5 |
| 13 | 8.5 | 21 | 30 |
| 14 | 6.0 | 23 | 30.5 |
| 15 | 9.0 | 22.5 | 31.5 |
| 16 | 4.0 | 22.5 | 31.5 |
| 17 | 3.0 | 21 | 30.5 |
| 18 | 12.0 | 20.5 | 30.5 |
| 19 | 4.0 | 20.5 | 30 |
| 20 | 4.0 | 20 | 30 |
| 21 | 12.0 | 20 | 30 |
| 22 | 9.0 | 20 | 31 |
| 23 | 3.0 | 21 | 31 |
| 24 | 12.0 | 19 | 29.5 |
| 25 | 4.0 | 19 | 29.5 |
| 26 | 4.0 | 18 | 29.5 |
| 27 | 9.0 | 19 | 29 |
| 28 | 12.0 | — | — |
| 29 | 4.0 | 18 | 28 |
| 30 | 4.0 | 18 | 27.5 |
| 31 | 12.0 | 17 | 28 |
| 32 | 12.0 | 17 | 27 |
| 33 | 12.0 | 17.5 | 26 |
| 34 | 12.0 | 17 | 26 |
| 35 | 10.0 | 17 | 25 |
| 36 | 12.0 | 17 | 25 |
| 37 | 7.0 | 15 | 24 |
| 38 | 12.0 | 15 | 23.5 |
| 39 | 12.0 | traces | 23.5 |
| 40 | 12.0 | 0 | 24 |
| 41 | 7.0 | 0 | 25 |
| 42 | 12.0 | 0 | — |
| 43 | 12.0 | 0 | — |

The following pools are made:
Pool I: Fractions 9-12 ca. 24 l
Pool II: Fractions 13-20 ca. 50.5 l
Pool III: Fractions 21-43 ca. 214 l Acanthomycin is isolated from the above pools by Amberlite XAD-7 chromatographies as described below.

(A) Isolation of Acanthomycin from Pool I

Amberlite XAD-7 Chromatography

The column is prepared from 1 l of Amberlite XAD-7. Pool I is adjusted to pH 3.0 with 6 N aqueous hydrochloric acid and passed over the column with a flow rate of 25 ml/minute. The spent is found bioinactive and is discarded. The column is then washed with 3 l of water. The aqueous wash is found bioinactive and is also discarded. The column is then eluted with methanol-water (70:30 v/v). Fractions of 20 ml are collected. Testing shows the following.

| Fraction No. | Zone (mm) B. subtilis | S. pyogenes |
|---|---|---|
| 10 | 0 | 0 |
| 20 | 0 | 0 |
| 30 | 0 | 0 |
| 40 | 0 | 0 |
| 50 | 20.5 | 23.5 |
| 60 | 25 | 29.5 |
| 70 | 26 | 32.5 |
| 80 | 27 | 34 |
| 90 | 26.5 | 34.5 |
| 100 | 26 | 34.5 |
| 110 | 25.5 | 33.5 |
| 120 | 25.5 | 32 |
| 130 | 24 | 31 |

-continued

| Fraction No. | Zone (mm) B. subtilis | S. pyogenes |
|---|---|---|
| 140 | 23 | 31 |
| 150 | 21.5 | 28.5 |
| 160 | 20 | 27.5 |
| 170 | 18 | 24.5 |
| 180 | 16 | 22 |
| 190 | 0 | 18 |
| 200 | 0 | 16 |
| 210 | 0 | 0 |
| 400 | 0 | 0 |

Fractions 46-200 are combined, adjusted to pH 7.5 with ammonium hydroxide, concentrated to an aqueous solution and freeze-dried to give preparation ADA-44.1, 550 mg (acanthomycin ammonium salt).

(B) Isolation of Acanthomycin from Pool II

Amberlite XAD-7 Chromatography

The column is prepared from 2 l of Amberlite XAD-7. Pool II is adjusted to pH 3.0 with 6 N aqueous hydrochloric acid. A precipitate is formed which is separated by filtration and dried (ADA-45). This material yields crystalline acanthomycin, as described infra. The filtrate is passed over the column at a rate of 50 ml/minute. The spent solution is found bioinactive and is discarded. The column is then washed with 6 l of water. The aqueous wash is found bioinactive and is also discarded. The column is then washed with 6 l of water. The aqueous wash is found bioinactive and is also discarded. The column is then eluted with methanol-water (70:30 v/v). Fractions (20 ml) are collected. Testing shows the following.

| Fraction No. | Zone(mm) B. subtilis | S. pyogenes |
|---|---|---|
| 10 | 0 | 0 |
| 20 | 0 | 0 |
| 140 | 0 | traces |
| 150 | 0 | 15 |
| 160 | 0 | 16 |
| 170 | 0 | 16 |
| 180 | 0 | 18 |
| 190 | 16 | 22 |
| 200 | 19 | 25 |
| 210 | 22 | 29 |
| 220 | 24 | 33.5 |
| 230 | 27 | 33.5 |
| 240 | 27.5 | 36 |
| 250 | 28.5 | 38 |
| 260 | 28 | 37.5 |
| 270 | 28 | 38.5 |
| 280 | 27 | 34.5 |
| 290 | 27 | 33.5 |
| 300 | 26 | 33 |
| 310 | 25.5 | 32 |
| 320 | 24 | 31 |
| 330 | 23.5 | 29 |
| 340 | 23 | 29.5 |
| 350 | 22 | 29 |
| 360 | 21 | 29 |
| 370 | 20.5 | 27.5 |
| 380 | 21 | 28 |
| 390 | 20 | 27 |
| 400 | 19.5 | 26 |
| 410 | 19.5 | 26 |
| 420 | 19 | 25 |
| 430 | 19 | 24 |
| 440 | 18 | 23 |
| 450 | 17 | 23.5 |
| 460 | 17 | 23 |

| Fraction No. | Zone(mm) B. subtilis | S. pyogenes |
|---|---|---|
| 470 | 17 | 23 |
| 480 | 16 | 22 |

The column is then eluted with methanol-0.05 N ammonium hydroxide. Fractions of 20 ml are collected. Results follow:

| Fraction No. | Zone (mm) B. subtilis | S. pyogenes |
|---|---|---|
| 10 | 15.5 | 21.5 |
| 20 | 15 | 21 |
| 30 | 15 | 21 |
| 40 | 16 | 20.5 |
| 50 | 16 | 19.5 |
| 60 | 15 | 17.5 |
| 70 | 15 | 19 |
| 80 | 15 | 20.5 |
| 90 | 17 | 23.5 |
| 100 | 20 | 27.5 |
| 110 | 25 | 33 |
| 120 | 26 | 34.5 |
| 130 | 20 | 25.5 |
| 140 | 0 | traces |

The following combinations are made:
I: Fractions (Methanol-water 70:30); 190–219
II: Fractions (Methanol-water 70:30); 220–399
III: Fractions (Methanol-water 70:30); 440–483
IV: Fractions (Methanol-0.05 NH4OH 70:30); 100–140

The combined solutions are concentrated to dryness to give the following:
I: Acanthomycin, prep. ADA-46.3; 70 mg
II: Acanthomycin, prep. ADA-46.4; 450 mg
III: Acanthomycin, prep. ADA-46.5; 50 mg
IV: Acanthomycin ammonium salt, prep. ADA-46.6; 250 mg As mentioned above, a precipitate, formed by acidification of pool II, is isolated by filtration and kept as ADA-45. Trituration of this material with methanol, followed by concentration of the methanolic solution to dryness, yields a crystalline residue. Trituration of the residue with ether affords colorless crystalline acanthomycin which is isolated by filtration and dried (Prep. ADA-46.1, 420 mg).

(C) Isolation of Acanthomycin from Pool III

Amberlite XAD-7 Chromatography

The column is prepared from 3 l of Amberlite XAD-7.

Starting material, Pool III, prepared as described above, is adjusted to pH 3.0 with 6 N aqueous hydrochloric acid and this solution is passed over the column at a flow rate of 75 ml/minute. The spent is found bioinactive and is discarded. The column is washed with 9 l of water. The aqueous wash is found bioinactive and is discarded. The column is eluted with methanol-water (70:30 v/v). Fractions (20 ml) are collected. Testing results follow.

| Fraction No. | Zone (mm) B. subtilis | S. pyogenes |
|---|---|---|
| 10 | 0 | 0 |
| 20 | 0 | 0 |
| 120 | 0 | 0 |
| 130 | 0 | 18 |
| 140 | 0 | 20 |
| 150 | traces | 23 |
| 160 | 16 | 27 |
| 170 | 17 | 30 |
| 180 | 19 | 31.5 |
| 190 | 21 | 33.5 |
| 200 | 22 | 34 |
| 210 | 24 | 35 |
| 220 | 25.5 | 36.5 |
| 230 | 26 | 37 |
| 240 | 27 | 38 |
| 250 | 27 | 39 |
| 260 | 27 | 38 |
| 270 | 27 | 39 |
| 280 | 27 | 39 |
| 290 | 27 | 39 |
| 300 | 27 | 39 |
| 310 | 27 | 38 |
| 320 | 28 | 37.5 |
| 330 | 27.5 | 37 |
| 340 | 27 | 37 |
| 350 | 26 | 37.5 |
| 360 | 26 | 37 |
| 370 | 25 | 37 |
| 380 | 24 | 36 |
| 390 | 24 | 36 |
| 400 | 24 | 34.5 |
| 420 | 24 | 34 |
| 440 | 23 | 33 |
| 460 | 22.5 | 32 |
| 480 | 22 | 32 |
| 500 | 22 | 31.5 |
| 520 | 21.5 | 31 |
| 540 | 21 | 30 |
| 560 | 20.5 | 31 |
| 580 | 21 | 31 |
| 600 | 21 | 30.5 |
| 620 | 21 | 31 |
| 640 | 21 | 30 |
| 660 | 20.5 | 31 |
| 680 | 21 | 31 |
| 700 | 21 | 31 |
| 720 | 21 | 31.5 |
| 740 | 21 | 31 |
| 760 | 21 | 31 |
| 780 | 20.5 | 30.5 |
| 800 | 20 | 30.5 |
| 820 | 19.5 | 30 |
| 840 | 19.5 | 30 |
| 860 | 19 | 29.5 |
| 880 | 18 | 29 |
| 900 | 18 | 28 |
| 920 | 18 | 28 |
| 940 | 18 | 28 |

The column is then eluted with methanol-0.05 N ammonium hydroxide. Fractions (20 ml) are collected and tested. Results follow.

| Fraction No. | Zone (mm) B. subtilis | S. pyogenes |
|---|---|---|
| 10 | 19 | 29 |
| 20 | 18 | 28.5 |
| 30 | 18 | 28 |
| 40 | 18 | 28 |
| 50 | 18 | 27 |
| 60 | 17 | 26 |
| 70 | 16 | 26 |
| 80 | 16 | 26 |
| 90 | 16 | 26 |
| 100 | 16.5 | 26 |
| 110 | 16 | 25.5 |
| 120 | 22 | 31 |

-continued

| Fraction No. | Zone (mm) B. subtilis | S. pyogenes |
| --- | --- | --- |
| 130 | 28 | 38 |
| 140 | 30.5 | 41 |
| 150 | 28 | 38 |
| 160 | 17.5 | 28.5 |
| 170 | 0 | 20.5 |
| 180 | 0 | 20.5 |
| 190 | 0 | 20.5 |
| 200 | 0 | 20 |
| 220 | 0 | 18 |
| 240 | 0 | 17.5 |
| 260 | 0 | 17 |
| 280 | 0 | 17 |
| 300 | 0 | 18 |
| 320 | 0 | 16.5 |
| 340 | 0 | 16 |
| 360 | 0 | 16.5 |
| 380 | 0 | 17 |
| 400 | 0 | 17.5 |
| 420 | 0 | 16 |
| 440 | 0 | 0 |
| 500 | 0 | 0 |

The following combinations are made:

Pool IA: Fractions 170–400 (methanol-water 70:30)

Pool IIA: Fractions 401–950 (methanol-water 70:30) and 10–100 (methanol-0.05 N NH$_4$OH)

Pool IIIA: Fractions 115–170 (methanol-0.05 N NH$_4$OH)

Pool IA is concentrated to dryness. The residue obtained is triturated with 50 ml of methanol. The colorless insoluble crystalline acanthomycin is isolated by filtration and dried (ADA-49.1, 210 mg). The filtrate is mixed with ether-Skellysolve B (isomeric hexanes) (1:1) to yield additional amorphous acanthomycin (ADA-49.2, 500 mg).

Pool IIA, similarly, yields crystalline acanthomycin, prep. ADA-49.3, 220 mg and amorphous acanthomycin, prep. ADA-49.4, 300 mg.

Pool IIIA is concentrated to an aqueous solution and then freeze-dried to give acanthomycin ammonium salt (prep. ADA-49.5, 800 mg).

We claim:

1. Antibiotic acanthomycin, which is active against S. aureus, and which in its essentially pure form
   (a) has the empirical formula: $(C_{90}H_{139}N_{19}O_{42})_n$;
   (b) has the following elemental analysis: C, 49.81; H, 6.47; N, 12.36; O (by difference), 31.36;
   (c) has an optical rotation $[\alpha]_D^{25}$, $-28.5°$ (c, 1, dimethylsulfoxide);
   (d) is soluble in dimethylformamide and dimethylsulfoxide; slightly soluble (ca. 1–2 mg/ml) in methanol and ethanol, and relatively insoluble in water, ether, halogenated hydrocarbon and saturated hydrocarbon solvents; and salts (ammonium and sodium) are soluble in water and lower alcohols;
   (e) has an equivalent weight of 2159;
   (f) has a characteristic infrared absorption spectrum when dissolved in a mineral oil mull as shown in FIG. 1 of the drawings; and,
   (g) has a characteristic ultraviolet absorption spectrum in methanol as shown in FIG. 2 of the drawings, and base addition salts thereof.

2. Ammonium salt of acanthomycin, according to claim 1.

3. A process for preparing acanthomycin which comprises cultivating Streptomyces espinosus subsp. acanthus, having the identifying characteristics of NRRL 11081, and mutants thereof, in an aqueous nutrient fermentation medium under aerobic conditions until substantial antibiotic activity is imparted to said fermentation medium, and recovering acanthomycin.

4. A biologically pure culture of the novel microorganism Streptomyces espinosus subsp. acanthus, having the identifying characteristics of NRRL 11081, said culture being capable of producing the antibiotic acanthomycin in a recoverable quantity upon fermentation in an aqueous nutrient medium containing assimilable sources of carbon, nitrogen and inorganic substances.

5. A process for recovering acanthomycin, according to claim 3, which comprises:
   (a) filtering an acanthomycin containing fermentation beer to obtain a clear beer;
   (b) extracting said clear beer with a solvent for acanthomycin to obtain a crude preparation of acanthomycin;
   (c) contacting said crude preparation of acanthomycin with ethyl acetate to give a precipitate containing acanthomycin;
   (d) distributing said precipitate between water and 1-butanol to give a butanol phase containing acanthomycin;
   (e) subjecting said butanol phase to chromatographic procedure on an anion exchanger to give fractions containing acanthomycin; and,
   (f) subjecting said fractions to chromatographic procedure on a non-ionic macro-porous copolymer of styrene crosslinked with divinylbenzene resin to give a purified preparation of acanthomycin.

6. A process, according to claim 5, wherein said anion exchange resin is Amberlite IRA-904 in the chloride form.

7. A process, according to claim 6, wherein said non-ionic resin Amberlite XAD-7.

* * * * *

UNITED STATES PATENT AND TRADEMARK OFFICE
CERTIFICATE OF CORRECTION

PATENT NO. : 4,259,450

DATED : March 31, 1981

INVENTOR(S) : Alexander D. Argoudelis, Thomas F. Brodasky, and Fritz Reusser

It is certified that error appears in the above—identified patent and that said Letters Patent is hereby corrected as shown below:

Column 1, line 13: "aerueus" should read -- aureus --.
Column 3, line 13: "S. pyogenese" should read -- S. pyogenes --
Column 3, line 49: "Stroptomyces" should read -- Streptomyces --
Column 4, Table 1, last column, third entry from bottom was omitted and should read -- pale gray --.
Column 6, Table 2, line 57: "gm" should read -- 90gm --.
Column 9, Table 4, last line in column entitled "NRRL 5729" reads "nitrate" and should read -- nitrite --.
Column 13, line 2: "conductive" should read -- conducive --.
Column 14, line 7: "preparaions" should read -- preparations --.
Column 15, line 3: "acanthus" should be italicized.

Signed and Sealed this

Third Day of November 1981

[SEAL]

Attest:

GERALD J. MOSSINGHOFF

Attesting Officer

Commissioner of Patents and Trademarks